United States Patent
Liang et al.

(10) Patent No.: US 9,877,856 B2
(45) Date of Patent: *Jan. 30, 2018

(54) METHODS AND APPARATUS FOR LUMINAL STENTING

(71) Applicant: Covidien LP, Mansfield, MA (US)

(72) Inventors: Jessica Liang, Irvine, CA (US); Jianlu Ma, Irvine, CA (US)

(73) Assignee: Covidien LP, Mansfield, MA (US)

(*) Notice: Subject to any disclaimer, the term of this patent is extended or adjusted under 35 U.S.C. 154(b) by 294 days.

This patent is subject to a terminal disclaimer.

(21) Appl. No.: 14/879,749

(22) Filed: Oct. 9, 2015

(65) Prior Publication Data

US 2016/0100968 A1    Apr. 14, 2016

Related U.S. Application Data

(63) Continuation of application No. 13/552,105, filed on Jul. 18, 2012, now Pat. No. 9,155,647.

(51) Int. Cl.
*A61F 2/966* (2013.01)
*A61F 2/962* (2013.01)
*A61F 2/95* (2013.01)

(52) U.S. Cl.
CPC ............ *A61F 2/962* (2013.01); *A61F 2/95* (2013.01); *A61F 2/966* (2013.01);
(Continued)

(58) Field of Classification Search
CPC .. A61F 2/95; A61F 2/962; A61F 2/966; A61F 2002/9505; A61F 2002/9665; A61F 2250/0043
See application file for complete search history.

(56) References Cited

U.S. PATENT DOCUMENTS 4,321,711 A    3/1982  Mano
4,503,569 A    3/1985  Dotter
(Continued)

FOREIGN PATENT DOCUMENTS

EP    418677 A1    3/1991
EP    442657 A2    8/1991
(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.
(Continued)

*Primary Examiner* — Ryan J Severson
*Assistant Examiner* — Christian Knauss
(74) *Attorney, Agent, or Firm* — Fortem IP LLP; Matthew Lincicum

(57) ABSTRACT

A stent delivery device includes a first retaining polymer disposed about and retaining a self-expanding stent at a proximal end portion, a second retaining polymer disposed about and retaining the self-expanding stent at a distal end portion, a first resistance member in thermal communication with the first retaining polymer, and a second resistance member in thermal communication with the second retaining polymer. The second retaining polymer and second resistance member are configured to allow release and expansion of the distal end portion of the self-expanding stent without expansion of the proximal end portion of the self-expanding stent.

18 Claims, 6 Drawing Sheets

(52) U.S. Cl.
CPC ............... *A61F 2002/9505* (2013.01); *A61F 2002/9665* (2013.01); *A61F 2250/0043* (2013.01)

(56) References Cited

U.S. PATENT DOCUMENTS

| | | | |
|---|---|---|---|
| 4,512,338 A | 4/1985 | Balko et al. |
| 4,538,622 A | 9/1985 | Samson et al. |
| 4,580,568 A | 4/1986 | Gianturco |
| 4,655,771 A | 4/1987 | Wallsten |
| 4,733,665 A | 3/1988 | Palmaz |
| 4,768,507 A | 9/1988 | Fischell et al. |
| 4,776,337 A | 10/1988 | Palmaz |
| 4,954,126 A | 9/1990 | Wallsten |
| 4,998,539 A | 3/1991 | Delsanti |
| 5,011,488 A | 4/1991 | Ginsburg |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,108,416 A | 4/1992 | Ryan et al. |
| 5,147,370 A | 9/1992 | McNamara et al. |
| 5,160,341 A | 11/1992 | Brenneman et al. |
| 5,180,368 A | 1/1993 | Garrison |
| 5,192,297 A | 3/1993 | Hull |
| 5,201,757 A | 4/1993 | Heyn et al. |
| 5,209,731 A | 5/1993 | Sterman et al. |
| 5,222,971 A | 6/1993 | Willard et al. |
| 5,242,399 A | 9/1993 | Lau et al. |
| 5,246,420 A | 9/1993 | Kraus et al. |
| 5,246,445 A | 9/1993 | Yachia et al. |
| 5,334,210 A | 8/1994 | Gianturco |
| 5,344,426 A | 9/1994 | Lau et al. |
| 5,360,443 A | 11/1994 | Barone et al. |
| 5,378,239 A | 1/1995 | Termin et al. |
| 5,382,259 A | 1/1995 | Phelps et al. |
| 5,401,257 A | 3/1995 | Chevalier, Jr. et al. |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,445,646 A | 8/1995 | Euteneuer et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,503,636 A | 4/1996 | Schmitt et al. |
| 5,507,768 A | 4/1996 | Lau et al. |
| 5,522,822 A | 6/1996 | Phelps et al. |
| 5,534,007 A | 7/1996 | St. Germain et al. |
| 5,549,635 A | 8/1996 | Solar |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,632,772 A | 5/1997 | Alcime et al. |
| 5,636,641 A | 6/1997 | Fariabi |
| 5,643,278 A | 7/1997 | Wijay |
| 5,662,703 A | 9/1997 | Yurek et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,725,552 A | 3/1998 | Kotula et al. |
| 5,725,570 A | 3/1998 | Heath |
| 5,725,571 A | 3/1998 | Imbert et al. |
| 5,733,294 A | 3/1998 | Forber et al. |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,749,883 A | 5/1998 | Halpern |
| 5,749,891 A | 5/1998 | Ken et al. |
| 5,749,919 A | 5/1998 | Blanc |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,140 A | 7/1998 | Cottone |
| 5,776,141 A | 7/1998 | Klein et al. |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,807,398 A | 9/1998 | Shaknovich |
| 5,810,837 A | 9/1998 | Hofmann et al. |
| 5,814,062 A | 9/1998 | Sepetka et al. |
| 5,817,102 A | 10/1998 | Johnson et al. |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,833,632 A | 11/1998 | Jacobsen et al. |
| 5,836,868 A | 11/1998 | Ressemann et al. |
| 5,846,261 A | 12/1998 | Kotula et al. |
| 5,868,754 A | 2/1999 | Levine et al. |
| 5,873,907 A * | 2/1999 | Frantzen ................. A61F 2/95 606/108 |
| 5,888,201 A | 3/1999 | Stinson et al. |
| 5,902,266 A | 5/1999 | Leone et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,916,235 A | 6/1999 | Guglielmi |
| 5,919,204 A | 7/1999 | Lukic et al. |
| 5,925,060 A | 7/1999 | Forber |
| 5,928,260 A | 7/1999 | Chin et al. |
| 5,935,148 A | 8/1999 | Villar et al. |
| 5,944,726 A | 8/1999 | Blaeser et al. |
| 5,944,738 A | 8/1999 | Amplatz et al. |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,972,015 A | 10/1999 | Scribner et al. |
| 5,980,530 A | 11/1999 | Willard et al. |
| 5,980,533 A | 11/1999 | Holman |
| 5,980,554 A | 11/1999 | Lenker et al. |
| 5,984,929 A | 11/1999 | Bashiri et al. |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |
| 6,024,763 A | 2/2000 | Lenker et al. |
| 6,027,516 A | 2/2000 | Kolobow et al. |
| 6,033,423 A | 3/2000 | Ken et al. |
| 6,036,720 A | 3/2000 | Abrams et al. |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,070 A | 5/2000 | Eder |
| 6,063,104 A | 5/2000 | Villar et al. |
| 6,063,111 A | 5/2000 | Hieshima et al. |
| 6,068,634 A | 5/2000 | Lorentzen Cornelius et al. |
| 6,074,407 A | 6/2000 | Levine et al. |
| 6,077,295 A | 6/2000 | Limon et al. |
| 6,086,577 A | 7/2000 | Ken et al. |
| 6,093,199 A | 7/2000 | Brown et al. |

(56) References Cited

U.S. PATENT DOCUMENTS

| | | |
|---|---|---|
| 6,096,052 A | 8/2000 | Callister et al. |
| 6,102,942 A | 8/2000 | Ahari |
| 6,113,607 A | 9/2000 | Lau et al. |
| 6,123,712 A | 9/2000 | Di Caprio et al. |
| 6,123,715 A | 9/2000 | Amplatz |
| 6,126,685 A | 10/2000 | Lenker et al. |
| 6,132,459 A | 10/2000 | Piplani et al. |
| 6,139,543 A | 10/2000 | Esch et al. |
| 6,139,564 A | 10/2000 | Teoh |
| 6,146,415 A | 11/2000 | Fitz |
| 6,149,680 A | 11/2000 | Shelso et al. |
| 6,152,144 A | 11/2000 | Lesh et al. |
| 6,165,178 A | 12/2000 | Bashiri et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,410 B1 | 2/2001 | Jacobsen et al. |
| 6,190,402 B1 | 2/2001 | Horton et al. |
| 6,193,708 B1 | 2/2001 | Ken et al. |
| 6,197,046 B1 | 3/2001 | Piplani et al. |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,086 B1 | 4/2001 | Forber |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,597 B1 | 5/2001 | Deem et al. |
| 6,235,050 B1 | 5/2001 | Quiachon et al. |
| 6,241,758 B1 | 6/2001 | Cox |
| 6,241,759 B1 | 6/2001 | Piplani et al. |
| 6,245,103 B1 | 6/2001 | Stinson |
| 6,251,132 B1 | 6/2001 | Ravenscroft et al. |
| 6,260,458 B1 | 7/2001 | Jacobsen et al. |
| 6,261,305 B1 | 7/2001 | Marotta et al. |
| 6,270,523 B1 | 8/2001 | Herweck et al. |
| 6,280,465 B1 | 8/2001 | Cryer |
| 6,287,331 B1 | 9/2001 | Heath |
| 6,290,721 B1 | 9/2001 | Heath |
| 6,302,810 B2 | 10/2001 | Yokota |
| 6,302,893 B1 | 10/2001 | Limon et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,331,184 B1 | 12/2001 | Abrams |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,348,063 B1 | 2/2002 | Yassour et al. |
| 6,350,199 B1 | 2/2002 | Williams et al. |
| 6,350,270 B1 | 2/2002 | Roue |
| 6,350,278 B1 | 2/2002 | Lenker et al. |
| 6,355,061 B1 | 3/2002 | Quiachon et al. |
| 6,368,339 B1 | 4/2002 | Amplatz |
| 6,368,344 B1 | 4/2002 | Fitz |
| 6,368,557 B1 | 4/2002 | Piplani et al. |
| 6,371,928 B1 | 4/2002 | Mcfann et al. |
| 6,375,668 B1 | 4/2002 | Gifford et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,383,174 B1 | 5/2002 | Eder |
| 6,387,118 B1 | 5/2002 | Hanson |
| 6,391,037 B1 | 5/2002 | Greenhalgh |
| 6,395,017 B1 | 5/2002 | Dwyer et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,536 B1 | 7/2002 | Yee |
| 6,428,489 B1 | 8/2002 | Jacobsen et al. |
| 6,428,558 B1 | 8/2002 | Jones et al. |
| 6,432,130 B1 | 8/2002 | Hanson |
| 6,440,088 B1 | 8/2002 | Jacobsen et al. |
| 6,443,971 B1 | 9/2002 | Boylan et al. |
| 6,443,979 B1 | 9/2002 | Stalker et al. |
| 6,447,531 B1 | 9/2002 | Amplatz |
| 6,451,025 B1 | 9/2002 | Jervis |
| 6,454,780 B1 | 9/2002 | Wallace |
| 6,454,999 B1 | 9/2002 | Farhangnia et al. |
| 6,468,266 B1 | 10/2002 | Bashiri et al. |
| 6,478,778 B1 | 11/2002 | Jacobsen et al. |
| 6,482,221 B1 | 11/2002 | Hebert et al. |
| 6,491,648 B1 | 12/2002 | Cornish et al. |
| 6,503,450 B1 | 1/2003 | Afzal et al. |
| 6,506,204 B2 | 1/2003 | Mazzocchi |
| 6,511,468 B1 | 1/2003 | Cragg et al. |
| 6,514,261 B1 | 2/2003 | Randall et al. |
| 6,520,983 B1 | 2/2003 | Colgan et al. |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine et al. |
| 6,547,804 B2 | 4/2003 | Porter et al. |
| 6,551,303 B1 | 4/2003 | Van Tassel et al. |
| 6,572,646 B1 | 6/2003 | Boylan et al. |
| 6,576,006 B2 | 6/2003 | Limon et al. |
| 6,579,303 B2 | 6/2003 | Amplatz |
| 6,582,460 B1 | 6/2003 | Cryer |
| 6,585,748 B1 | 7/2003 | Jeffree |
| 6,589,236 B2 | 7/2003 | Wheelock et al. |
| 6,589,256 B2 | 7/2003 | Forber |
| 6,589,265 B1 | 7/2003 | Palmer et al. |
| 6,589,273 B1 | 7/2003 | McDermott |
| 6,592,616 B1 | 7/2003 | Stack et al. |
| 6,599,308 B2 | 7/2003 | Amplatz |
| 6,602,280 B2 | 8/2003 | Chobotov |
| 6,605,102 B1 | 8/2003 | Mazzocchi et al. |
| 6,605,110 B2 | 8/2003 | Harrison |
| 6,605,111 B2 | 8/2003 | Bose et al. |
| 6,607,539 B1 * | 8/2003 | Hayashi ............... A61F 2/95 606/108 |
| 6,607,551 B1 | 8/2003 | Sullivan et al. |
| 6,613,074 B1 | 9/2003 | Miteiberg et al. |
| 6,613,075 B1 | 9/2003 | Healy et al. |
| 6,623,518 B2 | 9/2003 | Thompson et al. |
| 6,626,939 B1 | 9/2003 | Burnside et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,652,556 B1 | 11/2003 | VanTassel et al. |
| 6,656,212 B2 | 12/2003 | Ravenscroft et al. |
| 6,656,218 B1 | 12/2003 | Denardo et al. |
| 6,660,024 B1 | 12/2003 | Flaherty et al. |
| 6,663,666 B1 | 12/2003 | Quiachon et al. |
| 6,666,882 B1 | 12/2003 | Bose et al. |
| 6,669,719 B2 | 12/2003 | Wallace et al. |
| 6,669,721 B1 | 12/2003 | Bose et al. |
| 6,673,089 B1 | 1/2004 | Yassour et al. |
| 6,673,100 B2 | 1/2004 | Diaz et al. |
| 6,679,893 B1 | 1/2004 | Tran |
| 6,682,546 B2 | 1/2004 | Amplatz |
| 6,682,557 B1 | 1/2004 | Quiachon et al. |
| 6,685,735 B1 | 2/2004 | Ahari |
| 6,689,162 B1 | 2/2004 | Thompson |
| 6,689,486 B2 | 2/2004 | Ho et al. |
| 6,699,274 B2 | 3/2004 | Stinson |
| 6,709,454 B1 | 3/2004 | Cox et al. |
| 6,712,834 B2 | 3/2004 | Yassour et al. |
| 6,716,238 B2 | 4/2004 | Elliott |
| 6,726,700 B1 | 4/2004 | Levine |
| 6,730,108 B2 | 5/2004 | Van Tassel et al. |
| 6,733,519 B2 | 5/2004 | Lashinski et al. |
| 6,740,105 B2 | 5/2004 | Yodfat et al. |
| 6,740,112 B2 | 5/2004 | Yodfat et al. |

(56) References Cited

U.S. PATENT DOCUMENTS

| | | | |
|---|---|---|---|
| 6,743,219 | B1 | 6/2004 | Dwyer et al. |
| 6,746,468 | B1 | 6/2004 | Sepetka et al. |
| 6,746,890 | B2 | 6/2004 | Gupta et al. |
| 6,755,855 | B2 | 6/2004 | Yurek et al. |
| 6,758,885 | B2 | 7/2004 | Leffel et al. |
| 6,767,361 | B2 | 7/2004 | Quiachon et al. |
| 6,773,446 | B1 | 8/2004 | Dwyer et al. |
| 6,780,196 | B2 | 8/2004 | Chin et al. |
| 6,793,667 | B2 | 9/2004 | Hebert et al. |
| 6,802,851 | B2 | 10/2004 | Jones et al. |
| 6,811,560 | B2 | 11/2004 | Jones et al. |
| 6,814,748 | B1 | 11/2004 | Baker et al. |
| 6,818,006 | B2 | 11/2004 | Douk et al. |
| 6,830,575 | B2 * | 12/2004 | Stenzel ............... A61F 2/95 606/108 |
| 6,833,003 | B2 | 12/2004 | Jones et al. |
| 6,849,084 | B2 | 2/2005 | Rabkin et al. |
| 6,855,153 | B2 | 2/2005 | Saadat |
| 6,858,034 | B1 | 2/2005 | Hijlkema et al. |
| 6,860,893 | B2 | 3/2005 | Wallace et al. |
| 6,860,898 | B2 | 3/2005 | Stack et al. |
| 6,860,901 | B1 | 3/2005 | Baker et al. |
| 6,866,677 | B2 | 3/2005 | Douk et al. |
| 6,866,680 | B2 | 3/2005 | Yassour et al. |
| 6,887,267 | B2 | 5/2005 | Dworschak et al. |
| 6,890,337 | B2 | 5/2005 | Feeser et al. |
| 6,936,055 | B1 | 8/2005 | Ken et al. |
| 6,955,685 | B2 | 10/2005 | Escamilla et al. |
| 6,960,227 | B2 | 11/2005 | Jones et al. |
| 6,964,670 | B1 | 11/2005 | Shah et al. |
| 6,976,991 | B2 | 12/2005 | Hebert et al. |
| 6,989,024 | B2 | 1/2006 | Hebert et al. |
| 6,994,092 | B2 | 2/2006 | van der Burg et al. |
| 6,994,717 | B2 | 2/2006 | Konya et al. |
| 6,994,721 | B2 | 2/2006 | Israel |
| 7,001,422 | B2 | 2/2006 | Escamilla et al. |
| 7,004,964 | B2 | 2/2006 | Thompson et al. |
| 7,011,671 | B2 | 3/2006 | Welch |
| 7,011,675 | B2 | 3/2006 | Hemerick et al. |
| 7,029,487 | B2 | 4/2006 | Greene, Jr. et al. |
| 7,037,330 | B1 | 5/2006 | Rivelli, Jr. et al. |
| 7,066,951 | B2 | 6/2006 | Chobotov |
| 7,069,835 | B2 | 7/2006 | Nishri et al. |
| 7,074,236 | B2 | 7/2006 | Rabkin et al. |
| 7,083,632 | B2 | 8/2006 | Avellanet et al. |
| 7,093,527 | B2 | 8/2006 | Rapaport et al. |
| 7,101,392 | B2 | 9/2006 | Heath |
| 7,107,105 | B2 | 9/2006 | Bjorklund et al. |
| 7,118,539 | B2 | 10/2006 | Vrba et al. |
| 7,118,594 | B2 | 10/2006 | Quiachon et al. |
| 7,122,050 | B2 | 10/2006 | Randall et al. |
| 7,125,419 | B2 | 10/2006 | Sequin et al. |
| 7,128,073 | B1 | 10/2006 | van der Burg et al. |
| 7,128,736 | B1 | 10/2006 | Abrams et al. |
| 7,137,990 | B2 | 11/2006 | Hebert et al. |
| 7,166,125 | B1 | 1/2007 | Baker et al. |
| 7,169,170 | B2 | 1/2007 | Widenhouse |
| 7,169,172 | B2 | 1/2007 | Levine et al. |
| 7,169,177 | B2 | 1/2007 | Obara |
| 7,172,617 | B2 | 2/2007 | Colgan et al. |
| 7,195,636 | B2 | 3/2007 | Avellanet et al. |
| 7,195,639 | B2 | 3/2007 | Quiachon et al. |
| 7,195,648 | B2 | 3/2007 | Jones et al. |
| 7,201,768 | B2 | 4/2007 | Diaz et al. |
| 7,201,769 | B2 | 4/2007 | Jones et al. |
| 7,211,109 | B2 | 5/2007 | Thompson |
| 7,213,495 | B2 | 5/2007 | McCullagh et al. |
| 7,229,461 | B2 | 6/2007 | Chin et al. |
| 7,232,461 | B2 | 6/2007 | Ramer |
| 7,235,096 | B1 | 6/2007 | Van Tassel et al. |
| 7,264,632 | B2 | 9/2007 | Wright et al. |
| 7,275,471 | B2 | 10/2007 | Nishri et al. |
| 7,279,005 | B2 | 10/2007 | Stinson |
| 7,279,208 | B1 | 10/2007 | Goffena et al. |
| 7,294,137 | B2 | 11/2007 | Rivelli, Jr. et al. |
| 7,294,146 | B2 | 11/2007 | Chew et al. |
| 7,300,456 | B2 | 11/2007 | Andreas et al. |
| 7,300,460 | B2 | 11/2007 | Levine et al. |
| 7,306,624 | B2 | 12/2007 | Yodfat et al. |
| 7,309,351 | B2 | 12/2007 | Escamilla et al. |
| 7,311,031 | B2 | 12/2007 | McCullagh et al. |
| 7,320,702 | B2 | 1/2008 | Hammersmark et al. |
| 7,331,973 | B2 | 2/2008 | Gesswein et al. |
| 7,331,976 | B2 | 2/2008 | McGuckin, Jr. et al. |
| 7,331,980 | B2 | 2/2008 | Dubrul et al. |
| 7,331,985 | B2 | 2/2008 | Thompson et al. |
| 7,338,518 | B2 | 3/2008 | Chobotov |
| 7,419,503 | B2 | 9/2008 | Pulnev et al. |
| 7,468,070 | B2 | 12/2008 | Henry et al. |
| 7,470,282 | B2 | 12/2008 | Shelso |
| 7,473,271 | B2 | 1/2009 | Gunderson |
| 7,491,224 | B2 | 2/2009 | Cox et al. |
| 7,578,826 | B2 | 8/2009 | Gandhi et al. |
| 7,597,704 | B2 | 10/2009 | Frazier et al. |
| 7,785,361 | B2 | 8/2010 | Nikolchev et al. |
| 7,862,602 | B2 | 1/2011 | Licata et al. |
| 8,114,154 | B2 | 2/2012 | Righini et al. |
| 8,147,534 | B2 | 4/2012 | Berez et al. |
| 8,192,480 | B2 | 6/2012 | Tieu et al. |
| 8,206,431 | B2 | 6/2012 | Seppala et al. |
| 8,236,042 | B2 | 8/2012 | Berez et al. |
| 8,257,421 | B2 | 9/2012 | Berez et al. |
| 8,267,985 | B2 | 9/2012 | Garcia et al. |
| 8,273,101 | B2 | 9/2012 | Garcia et al. |
| 9,155,647 | B2 | 10/2015 | Liang et al. |
| 2001/0000797 | A1 | 5/2001 | Mazzocchi |
| 2001/0012949 | A1 | 8/2001 | Forber |
| 2001/0012961 | A1 | 8/2001 | Deem et al. |
| 2001/0049547 | A1 | 12/2001 | Moore |
| 2002/0013618 | A1 | 1/2002 | Marotta et al. |
| 2002/0062091 | A1 | 5/2002 | Jacobsen et al. |
| 2002/0078808 | A1 | 6/2002 | Jacobsen et al. |
| 2002/0087119 | A1 | 7/2002 | Parodi |
| 2002/0099405 | A1 | 7/2002 | Yurek et al. |
| 2002/0120323 | A1 | 8/2002 | Thompson et al. |
| 2002/0143384 | A1 | 10/2002 | Ozasa |
| 2002/0165572 | A1 | 11/2002 | Saadat |
| 2002/0169473 | A1 | 11/2002 | Sepetka et al. |
| 2002/0188341 | A1 | 12/2002 | Elliott |
| 2003/0028209 | A1 | 2/2003 | Teoh et al. |
| 2003/0057156 | A1 | 3/2003 | Peterson et al. |
| 2003/0069522 | A1 | 4/2003 | Jacobsen et al. |
| 2003/0100945 | A1 | 5/2003 | Yodfat et al. |
| 2003/0109887 | A1 | 6/2003 | Galdonik et al. |
| 2003/0135258 | A1 | 7/2003 | Andreas et al. |
| 2003/0149465 | A1 | 8/2003 | Heidner et al. |
| 2003/0163155 | A1 | 8/2003 | Haverkost et al. |
| 2003/0163156 | A1 | 8/2003 | Hebert et al. |
| 2003/0171739 | A1 | 9/2003 | Murphy et al. |
| 2003/0195553 | A1 | 10/2003 | Wallace et al. |
| 2003/0199913 | A1 | 10/2003 | Dubrul et al. |
| 2003/0208256 | A1 | 11/2003 | DiMatteo et al. |
| 2003/0216693 | A1 | 11/2003 | Mickley |
| 2004/0024416 | A1 | 2/2004 | Yodfat et al. |
| 2004/0044391 | A1 | 3/2004 | Porter |
| 2004/0044395 | A1 | 3/2004 | Nelson |
| 2004/0049204 | A1 | 3/2004 | Harari et al. |
| 2004/0049256 | A1 | 3/2004 | Yee |
| 2004/0059407 | A1 | 3/2004 | Escamilla et al. |
| 2004/0073300 | A1 | 4/2004 | Chouinard et al. |
| 2004/0078071 | A1 | 4/2004 | Escamilla et al. |
| 2004/0093010 | A1 | 5/2004 | Gesswein et al. |
| 2004/0093063 | A1 | 5/2004 | Wright et al. |
| 2004/0098028 | A1 | 5/2004 | Martinez |
| 2004/0122468 | A1 | 6/2004 | Yodfat et al. |
| 2004/0127912 | A1 | 7/2004 | Rabkin et al. |
| 2004/0138733 | A1 | 7/2004 | Weber et al. |
| 2004/0143286 | A1 | 7/2004 | Johnson et al. |
| 2004/0186551 | A1 | 9/2004 | Kao et al. |
| 2004/0186562 | A1 | 9/2004 | Cox |
| 2004/0193178 | A1 | 9/2004 | Nikolchev |
| 2004/0193179 | A1 | 9/2004 | Nikolchev |
| 2004/0193206 | A1 | 9/2004 | Gerberding et al. |
| 2004/0199243 | A1 | 10/2004 | Yodfat |

(56) References Cited

U.S. PATENT DOCUMENTS

| | | |
|---|---|---|
| 2004/0204749 A1 | 10/2004 | Gunderson |
| 2004/0215332 A1 | 10/2004 | Frid |
| 2004/0220585 A1 | 11/2004 | Nikolchev |
| 2005/0010281 A1 | 1/2005 | Yodfat et al. |
| 2005/0033408 A1 | 2/2005 | Jones et al. |
| 2005/0033409 A1 | 2/2005 | Burke et al. |
| 2005/0049668 A1 | 3/2005 | Jones et al. |
| 2005/0049670 A1* | 3/2005 | Jones .................. A61F 2/91 623/1.12 |
| 2005/0090890 A1 | 4/2005 | Wu et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131523 A1* | 6/2005 | Bashiri .................. A61F 2/90 623/1.15 |
| 2005/0137680 A1 | 6/2005 | Ortiz et al. |
| 2005/0209672 A1 | 9/2005 | George et al. |
| 2005/0209674 A1 | 9/2005 | Kutscher et al. |
| 2005/0228434 A1 | 10/2005 | Amplatz et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0283222 A1 | 12/2005 | Betelia et al. |
| 2005/0288764 A1 | 12/2005 | Snow et al. |
| 2005/0288766 A1 | 12/2005 | Plain et al. |
| 2006/0025845 A1 | 2/2006 | Escamilla et al. |
| 2006/0036309 A1 | 2/2006 | Hebert et al. |
| 2006/0052815 A1 | 3/2006 | Fitz et al. |
| 2006/0052816 A1 | 3/2006 | Bates et al. |
| 2006/0058865 A1 | 3/2006 | Case et al. |
| 2006/0064151 A1 | 3/2006 | Guterman et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116714 A1 | 6/2006 | Sepetka et al. |
| 2006/0116750 A1 | 6/2006 | Hebert et al. |
| 2006/0155323 A1 | 7/2006 | Porter et al. |
| 2006/0167494 A1 | 7/2006 | Suddaby |
| 2006/0184238 A1 | 8/2006 | Kaufmann et al. |
| 2006/0190076 A1 | 8/2006 | Taheri |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0235464 A1 | 10/2006 | Avellanet et al. |
| 2006/0235501 A1 | 10/2006 | Igaki |
| 2006/0247680 A1 | 11/2006 | Amplatz et al. |
| 2006/0271149 A1 | 11/2006 | Berez et al. |
| 2006/0271153 A1 | 11/2006 | Garcia et al. |
| 2007/0021816 A1 | 1/2007 | Rudin |
| 2007/0043419 A1 | 2/2007 | Nikolchev et al. |
| 2007/0055339 A1 | 3/2007 | George et al. |
| 2007/0073379 A1 | 3/2007 | Chang |
| 2007/0088387 A1 | 4/2007 | Eskridge et al. |
| 2007/0100414 A1 | 5/2007 | Licata et al. |
| 2007/0106311 A1 | 5/2007 | Wallace et al. |
| 2007/0112415 A1 | 5/2007 | Bartlett |
| 2007/0119295 A1 | 5/2007 | McCullagh et al. |
| 2007/0123969 A1 | 5/2007 | Gianotti |
| 2007/0162104 A1 | 7/2007 | Frid |
| 2007/0167980 A1 | 7/2007 | Figulla et al. |
| 2007/0173928 A1 | 7/2007 | Morsi |
| 2007/0191884 A1 | 8/2007 | Eskridge et al. |
| 2007/0198075 A1 | 8/2007 | Levy |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0203567 A1 | 8/2007 | Levy |
| 2007/0208376 A1 | 9/2007 | Meng |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0003354 A1 | 1/2008 | Nolan |
| 2008/0021535 A1 | 1/2008 | Leopold et al. |
| 2008/0039933 A1 | 2/2008 | Yodfat et al. |
| 2008/0082154 A1 | 4/2008 | Tseng et al. |
| 2008/0097495 A1 | 4/2008 | Feller, III et al. |
| 2008/0119886 A1 | 5/2008 | Greenhalgh et al. |
| 2008/0154286 A1 | 6/2008 | Abbott et al. |
| 2008/0195139 A1 | 8/2008 | Donald et al. |
| 2008/0208320 A1 | 8/2008 | Tan-Malecki et al. |
| 2008/0219533 A1 | 9/2008 | Grigorescu |
| 2008/0221600 A1 | 9/2008 | Dieck et al. |
| 2008/0221666 A1 | 9/2008 | Licata et al. |
| 2008/0255654 A1 | 10/2008 | Hebert et al. |
| 2008/0262590 A1 | 10/2008 | Murray |
| 2008/0269774 A1 | 10/2008 | Garcia et al. |
| 2008/0281350 A1 | 11/2008 | Sepetka et al. |
| 2008/0300667 A1 | 12/2008 | Hebert et al. |
| 2008/0319533 A1 | 12/2008 | Lehe |
| 2009/0024202 A1 | 1/2009 | Dave et al. |
| 2009/0024205 A1 | 1/2009 | Hebert et al. |
| 2009/0025820 A1 | 1/2009 | Adams |
| 2009/0030496 A1 | 1/2009 | Kaufmann et al. |
| 2009/0030497 A1 | 1/2009 | Metcalf et al. |
| 2009/0082803 A1 | 3/2009 | Adams et al. |
| 2009/0105802 A1 | 4/2009 | Henry et al. |
| 2009/0105803 A1 | 4/2009 | Shelso |
| 2009/0112251 A1 | 4/2009 | Qian et al. |
| 2009/0125093 A1 | 5/2009 | Hansen |
| 2009/0138065 A1 | 5/2009 | Zhang et al. |
| 2009/0163986 A1 | 6/2009 | Tieu et al. |
| 2009/0192536 A1 | 7/2009 | Berez et al. |
| 2009/0198318 A1 | 8/2009 | Berez et al. |
| 2009/0210047 A1 | 8/2009 | Amplatz et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287292 A1 | 11/2009 | Becking et al. |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0030220 A1 | 2/2010 | Truckai et al. |
| 2010/0069948 A1 | 3/2010 | Veznedaroglu et al. |
| 2010/0152767 A1 | 6/2010 | Greenhalgh et al. |
| 2010/0268204 A1 | 10/2010 | Tieu et al. |
| 2010/0305606 A1 | 12/2010 | Gandhi et al. |
| 2010/0331948 A1 | 12/2010 | Turovskiy et al. |
| 2011/0313447 A1 | 12/2011 | Strauss et al. |
| 2012/0041470 A1 | 2/2012 | Shrivastava et al. |
| 2012/0041474 A1 | 2/2012 | Eckhouse et al. |
| 2012/0065720 A1 | 3/2012 | Strauss et al. |
| 2012/0221095 A1 | 8/2012 | Berez et al. |
| 2012/0277784 A1 | 11/2012 | Berez et al. |
| 2012/0283765 A1 | 11/2012 | Berez et al. |
| 2012/0283815 A1 | 11/2012 | Berez et al. |
| 2013/0144380 A1 | 6/2013 | Quadri et al. |
| 2013/0172925 A1 | 7/2013 | Garcia et al. |
| 2013/0172976 A1 | 7/2013 | Garcia et al. |

FOREIGN PATENT DOCUMENTS

| | | |
|---|---|---|
| EP | 696447 A2 | 2/1996 |
| EP | 1369098 A1 | 12/2003 |
| EP | 1400219 A1 | 3/2004 |
| EP | 1621148 A1 | 2/2006 |
| EP | 2 143 404 A1 | 1/2010 |
| EP | 2 143 460 A1 | 1/2010 |
| JP | 10-328216 A | 12/1998 |
| JP | 11-299901 A | 11/1999 |
| JP | 2001-509412 A | 7/2001 |
| JP | 2005-074230 A | 3/2005 |
| WO | WO-95/09586 A1 | 4/1995 |
| WO | WO-97/26939 A1 | 7/1997 |
| WO | WO-98/09583 A2 | 3/1998 |
| WO | WO-99/02092 A1 | 1/1999 |

(56) References Cited

FOREIGN PATENT DOCUMENTS

| WO | WO-99/03404 A1 | 1/1999 |
|---|---|---|
| WO | WO-99/05977 A1 | 2/1999 |
| WO | WO-99/049812 A3 | 12/1999 |
| WO | WO-99/62432 A1 | 12/1999 |
| WO | WO-00/13593 A1 | 3/2000 |
| WO | WO-2001/005331 A1 | 1/2001 |
| WO | WO-01/93782 A1 | 12/2001 |
| WO | WO-02/00139 | 1/2002 |
| WO | WO-02/28320 A2 | 4/2002 |
| WO | WO-02/056798 A2 | 7/2002 |
| WO | WO-02/60345 A2 | 8/2002 |
| WO | WO-02/71977 A2 | 9/2002 |
| WO | WO-03/007840 A2 | 1/2003 |
| WO | WO-03/022124 A2 | 3/2003 |
| WO | WO-2003/049600 A3 | 10/2003 |
| WO | WO-2004/010878 A1 | 2/2004 |
| WO | WO-2004/030575 A1 | 4/2004 |
| WO | WO-2004/066809 A2 | 8/2004 |
| WO | WO-2004/087006 A3 | 11/2004 |
| WO | WO-2005/018728 A2 | 3/2005 |
| WO | WO-2005/030093 A1 | 4/2005 |
| WO | WO-2005/117718 A1 | 12/2005 |
| WO | WO-2006/026744 A1 | 3/2006 |
| WO | WO-2006/052322 A2 | 5/2006 |
| WO | WO-2006/091891 A2 | 8/2006 |
| WO | WO-2006/127005 A1 | 11/2006 |
| WO | WO-2007/121405 | 10/2007 |
| WO | WO-2008/022327 A2 | 2/2008 |
| WO | WO-2008/157507 A2 | 12/2008 |
| WO | WO-2008151204 A1 | 12/2008 |
| WO | WO-2005/115118 A3 | 7/2009 |
| WO | WO-2009/134337 A1 | 11/2009 |
| WO | WO-2010/030991 A1 | 3/2010 |
| WO | WO-2011/130081 A1 | 10/2011 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Ameurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar. 1990, vol. Supplementum 48, pp. in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

Hill, et al., "Initial Results of the Amplatzer Vascular Plug in the Treatment of Congenital Heart Disease, Business Briefing" US Cardiology, 2004.

Ronen, "Amplatzer Vascular Plug Case Study, Closure of Arteriovenous Fistula Between Deep Femoral Artery and Superficial Femoral Vein," AGA Medical Corporation, May 2007.

\* cited by examiner

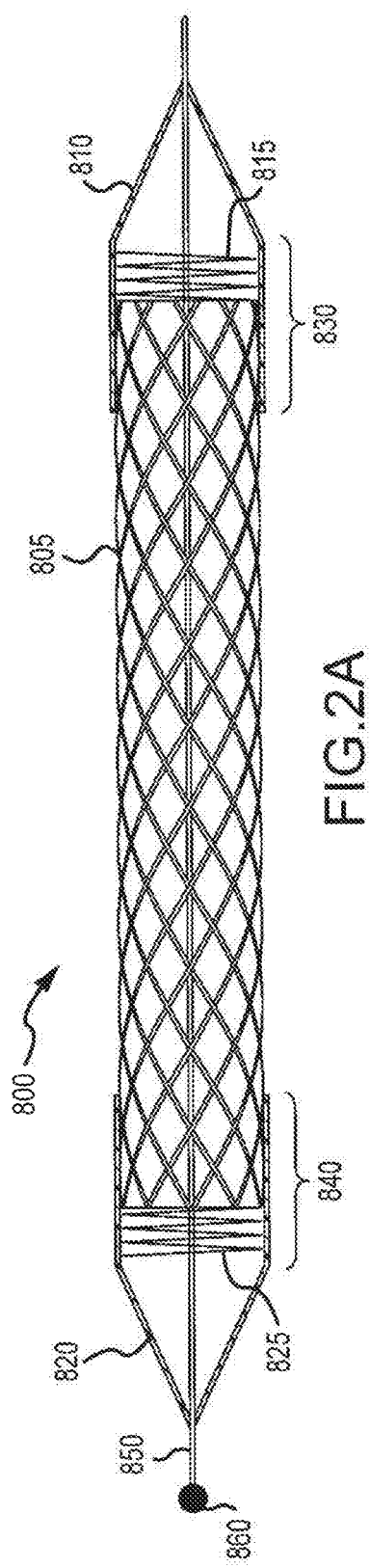
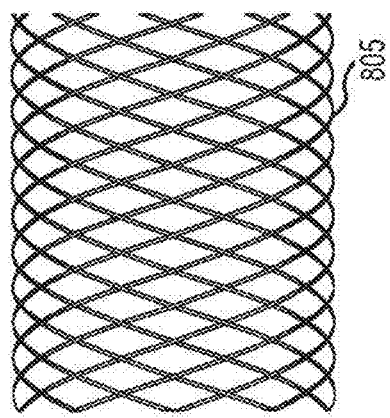
FIG.2A
FIG.2B

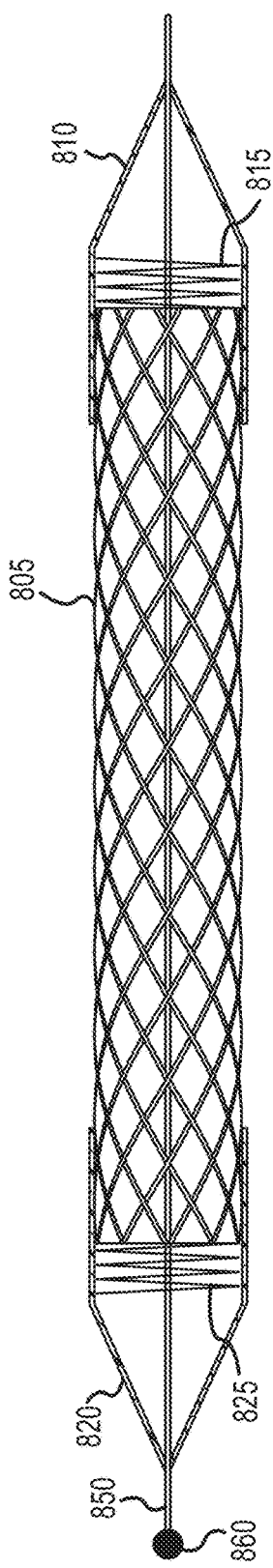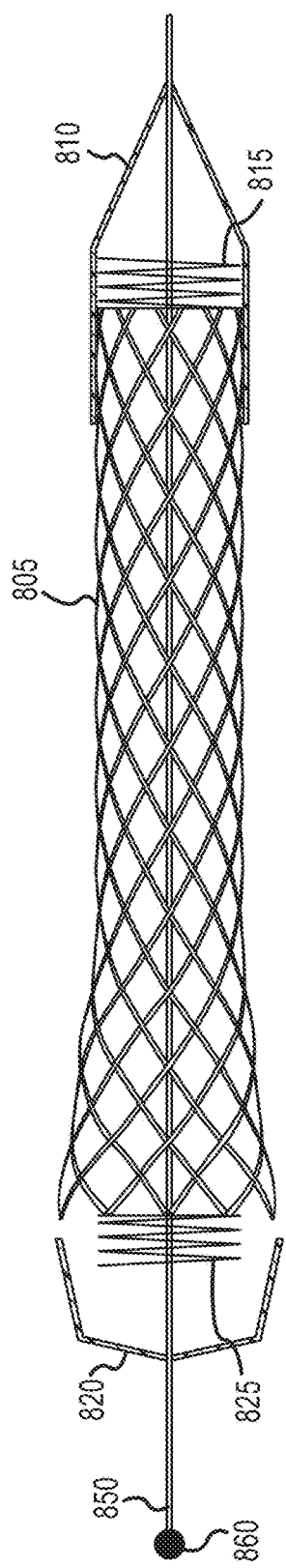
FIG.4A
FIG.4B

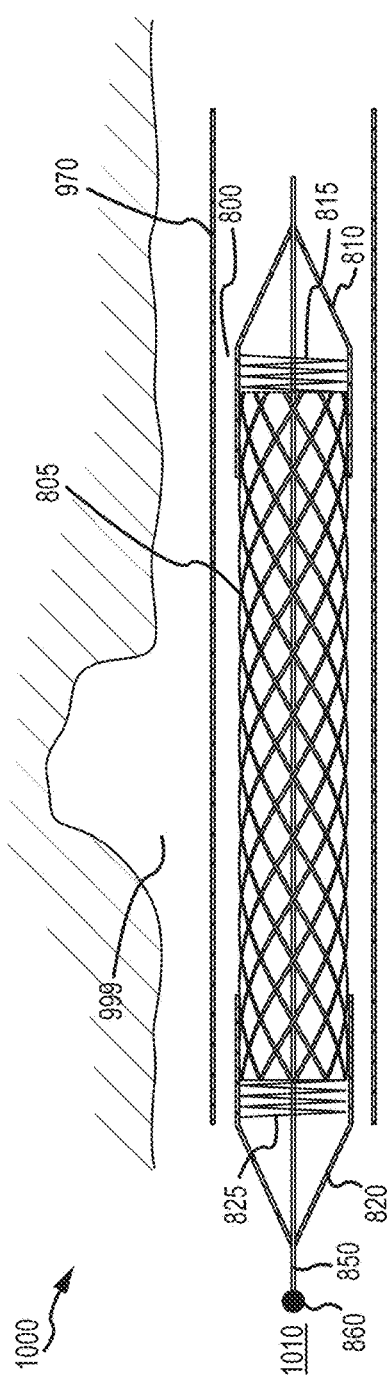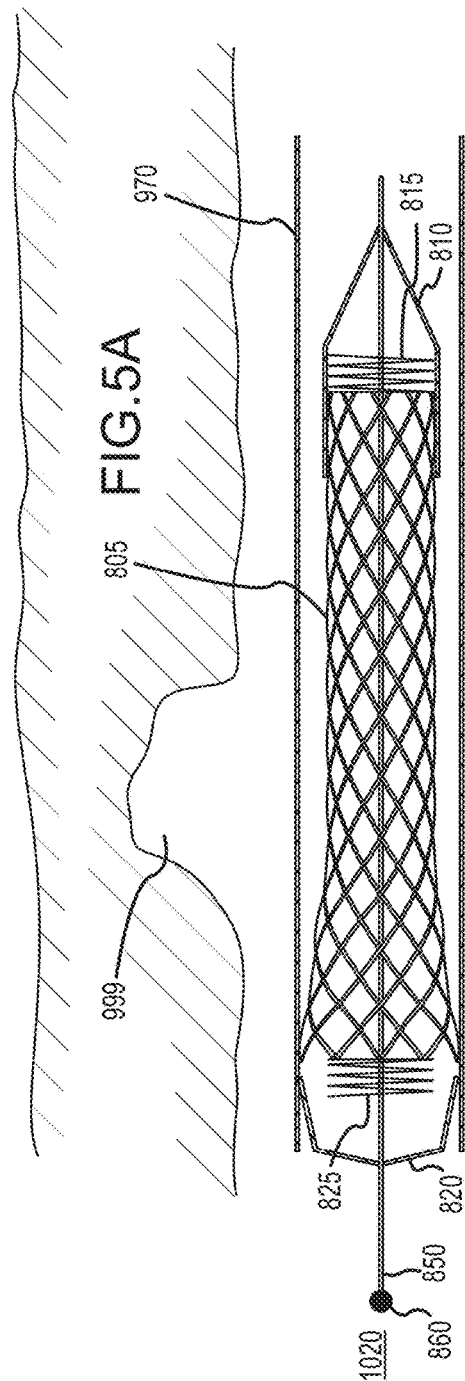

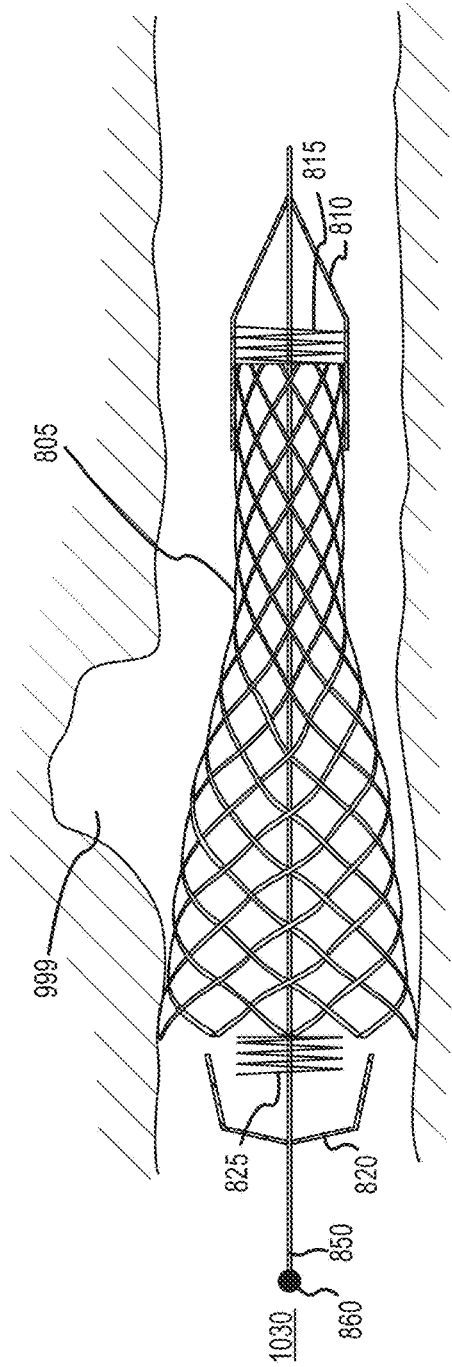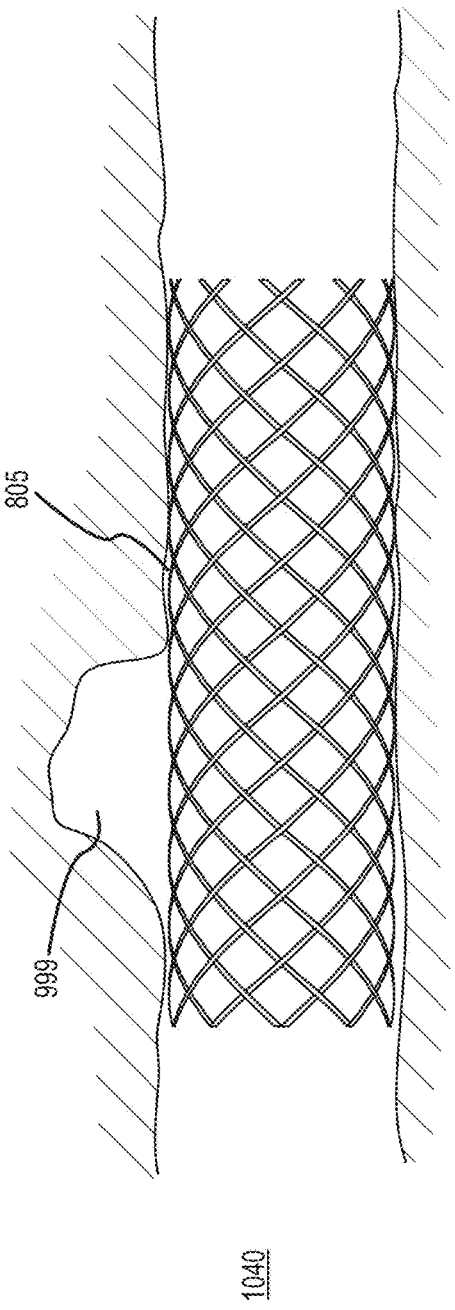

METHODS AND APPARATUS FOR LUMINAL STENTING

CROSS-REFERENCE TO RELATED APPLICATIONS

This application is a continuation of U.S. patent application Ser. No. 13/552,105, filed on Jul. 18, 2012, which is hereby incorporated by reference in its entirety.

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning-out of the wall of an artery. This is a result of the vessel wall being weakened by disease, injury or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, a ruptured aneurysm can also result in death.

Vascular devices or "occluding devices" such as stents are often used to treat patients with aneurysms. Stent and/or other occluding devices can be implanted within the vasculature of a patient by a delivery system such as a catheter. Precise and accurate positioning of these vascular devices at a target site is often required before a stent can be safely and effectively detached from the stent delivery system to a target site within a patient's vasculature. Positioning can be a delicate process that may require positioning and re-positioning of the stent delivery device prior to the detachment of the stent.

SUMMARY

In some aspects, embodiments disclosed herein relate to a stent delivery device comprising a first retaining polymer disposed about and retaining a proximal end portion of a self-expanding stent when the stent is in a compressed configuration, a second retaining polymer disposed about and retaining a distal end portion of the self-expanding stent in the compressed configuration, a first resistance member in thermal communication with the first retaining polymer, and a second resistance member in thermal communication with the second retaining polymer, wherein the second retaining polymer and second resistance member are configured to permit expansion of the distal end portion of the self-expanding stent to an expanded configuration without expansion of the proximal end portion of the self-expanding stent.

In some aspects, embodiments disclosed herein relate to a system for stent delivery comprising a self-expanding stent having a proximal end portion, a distal end portion, and a lumen, a push wire extending through the lumen, a first retaining polymer disposed about and retaining the proximal end portion in a compressed configuration, a second retaining polymer disposed about and retaining the distal end portion in a compressed configuration, a first resistance member in thermal communication with the first retaining polymer, and a second resistance member in thermal communication with the second retaining polymer, wherein the push wire is configured to deliver a current to the first and second resistance members, wherein each of the first and second retaining polymers are configured to disengage from the stent in response to different levels of applied current, thereby permitting expansion of the respective proximal and distal end portions to an expanded configuration.

In some aspects, embodiments disclosed herein relate to a method of delivering a stent comprising introducing a stent delivery device via catheter to a desired treatment location in a subject; said stent delivery device comprising a first retaining polymer disposed about and retaining a proximal end portion of a self-expanding stent when the stent is in a compressed configuration, a second retaining polymer disposed about and retaining a distal end portion of the self-expanding stent in the compressed configuration, a first resistance member in thermal communication with the first retaining polymer, and a second resistance member in thermal communication with the second retaining polymer, wherein the second retaining polymer and second resistance member are configured to permit expansion of the distal end portion of the self-expanding stent to an expanded configuration without expansion of the proximal end portion of the self-expanding stent, and applying a current to the second resistance member to release and expand the distal end portion.

In some aspects, embodiments disclosed herein relate to a method of treating an aneurysm comprising introducing a stent delivery device via catheter in the vicinity of an aneurysm in a subject; the stent delivery device comprising a first retaining polymer disposed about and retaining a self-expanding stent at a proximal end, a second retaining polymer disposed about and retaining the self-expanding stent at a distal end, a first resistance member in thermal communication with the first retaining polymer, and a second resistance member in thermal communication with the second retaining polymer, the second retaining polymer and second resistance member are configured to allow release and deployment of the distal end of the self-expanding stent without release of the proximal end of the self-expanding stent from the first retaining polymer; and the method further comprising applying a current to the second resistance member to release and deploy the distal end of the self-expanding stent.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 2A shows a delivery device having resistive heating elements in thermal contact with selectively and sequentially removable first and second retaining polymer members. The first and second retaining polymer members hold the stent in a longitudinally extended form against the force of longitudinal contraction and radial expansion.

FIG. 2B shows the stent of FIG. 2A after it has been released from the delivery device. As the stent expands radially, there is significant longitudinal contraction.

FIGS. 4A and 4B show the selective removal of the distal second retaining polymer of the device of FIG. 2A allowing selective deployment of the self-expanding stent at the distal end. FIG. 4A shows a stent held in place by a proximal first retaining polymer and a distal second retaining polymer. FIG. 4B shows the deployment of the distal end of the stent after selective removal of the distal second retaining polymer.

FIGS. 5A-D show a method of employing the system of FIG. 3A at the site of an aneurysm. FIG. 5A shows a stent delivery system with catheter delivery of a stent held in place by a proximal first retaining polymer and a distal second retaining polymer. FIG. 5B shows the deployment of the distal end of the stent after selective removal of the distal second retaining polymer, with the system still in place within the catheter, allowing for any adjustment for positioning of the stent. FIG. 5C shows the system after removal of the delivery catheter with the distal end of the stent now deployed at one end the aneurysm. FIG. 5D shows the fully deployed stent screening off the aneurysm after release of the proximal first polymer and removal of the guidewire.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
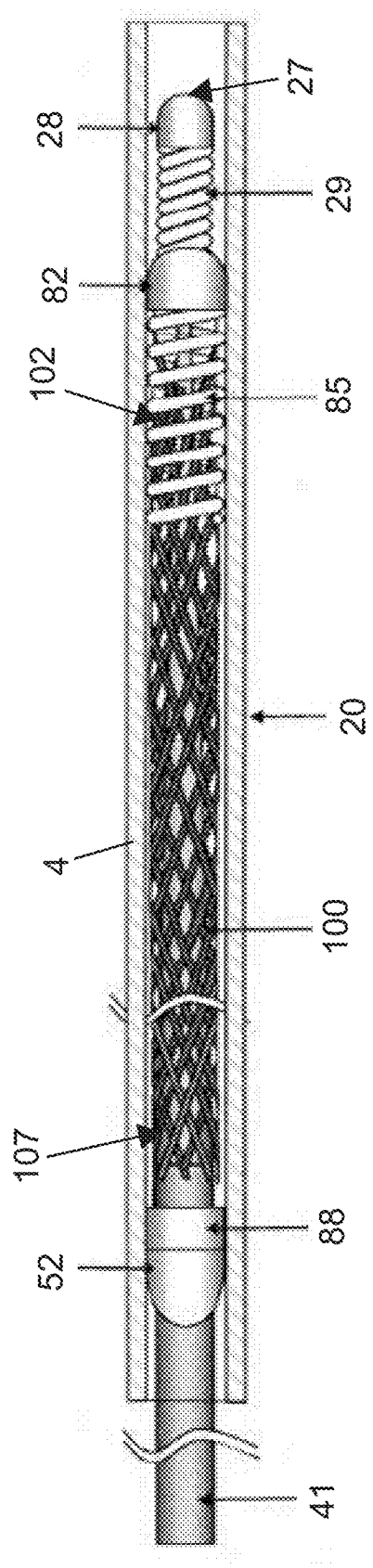
FIG. 1 is a partial cross-sectional view of an exemplary stent delivery system, according to one or more embodiments disclosed.

Described herein are various embodiments of stent delivery systems exhibiting small cross-sections which are highly flexible. Referring to FIG. 1, illustrated is an exemplary stent delivery system 20 including a stent 100 carried by a core wire 41 as arranged within an introducer sheath or catheter 4. The stent 100 and the core wire 41 may be cooperatively movable within the catheter 4 in order to deliver the stent 100 to a predetermined treatment site, such as an aneurysm, within the vasculature of a patient. Accordingly, the catheter 4 may be configured to be introduced and advanced through the vasculature of the patient. The catheter 4 may be made from various thermoplastics, e.g., PTFE, FEP, HDPE, PEEK, etc., which may optionally be lined on the inner surface of the catheter 4 or an adjacent surface with a hydrophilic material such as PVP or some other plastic coating. Additionally, either surface may be coated with various combinations of different materials, depending upon the desired results.

The stent 100 may be characterized as a vascular occluding device and/or an embolization device, as generally known in the art. These terms are broad terms and are intended to have their ordinary meaning and include, unless expressly otherwise stated or incompatible with the description of, each of the stents and other vascular devices described herein. In some embodiments, the stent 100 may be a self-expanding stent made of two or more round or ovoid wire filaments. The filaments may be formed of known flexible materials including shape memory materials, such as nitinol, platinum, and stainless steel. In some embodiments, the stent 100 is fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments may be braided into a resulting lattice-like structure. In at least one embodiment, during braiding or winding of the stent 100, the filaments may be loosely braided using a 1-over-2-under-2 system. In other embodiments, however, other methods of braiding may be followed, without departing from the scope of the disclosure. The stent 100 may exhibit a porosity configured to reduce haemodynamic flow into, for example, an aneurysm, but simultaneously allow perfusion to an adjacent branch vessel. As will be appreciated, the porosity of the stent 100 may be adjusted by "packing" the stent during deployment, as known in the art. The ends of the stent 100 may be cut to length and therefore remain free for radial expansion and contraction. The stent 100 may exhibit a high degree of flexibility due to the materials used, the density (i.e., the porosity) of the filaments, and the fact that the ends are not secured.

The flexibility of the core wire 41 allows the stent delivery system 20 to bend and conform to the curvature of the vasculature as needed for positional movement of the stent 100 within the vasculature. The core wire 41 may be made of a conventional guidewire material and have a solid cross-section. Alternatively, the core wire 41 can be formed from a hypotube. The material used for the core wire 41 can be any of the known guidewire materials including super-elastic metals or shape memory alloys, e.g., nitinol. Alternatively, the core wire 41 can be formed of metals such as stainless steel.

In one or more embodiments, the stent delivery system 20 may exhibit the same degree of flexion along its entire length. In other embodiments, however, the stent delivery system 20 can have two or more longitudinal sections, each with differing degrees of flexion/stiffness. The different degrees of flexions for the stent delivery system 20 can be created using different materials and/or thicknesses within different longitudinal sections of the core wire 41. In some embodiments, the flexion of the core wire 41 can be controlled by spaced cuts (not shown) formed within the core wire 41. These cuts can be longitudinally and/or circumferentially spaced from each other.

A tip 28 and flexible tip coil 29 may be secured to the distal end 27 of the delivery core wire 41. The tip 28 can be characterized as a distal solder joint formed of a continuous end cap or cover as shown in the figures, which securely receives a distal end of the tip coil 29. Flexion control is provided to the distal end 27 of the delivery core wire 41 by the tip coil 29. However, in an embodiment, the tip 28 can be free of the coil 29. As illustrated, the tip 28 may have a non-percutaneous, atraumatic end face. The tip coil 29 may be configured to surround at least a portion of the core wire 41. The tip coil 29 is flexible so that it will conform to and follow the path of a vessel within the patient as the tip 28 is advanced along the vessel and the core wire 41 bends to follow the tortuous path of the vasculature.

At the proximal end 107 of the stent 100, a proximal solder joint 52 and proximal marker 88 prevent or limit lateral movement of the stent 100 along the length of the core wire 41 in the direction of the proximal end 107. As illustrated, the proximal end 107 of the stent 100 may be axially-offset from the proximal marker 88 by a short distance. In other embodiments, however, the stent 100 may shift axially during introduction into the vasculature of the patient and contact the proximal marker 88 which prevents or limits the stent 100 from moving along the length of the core wire 41 away from a distally-located protective coil 85 coupled to an adjacent or mid solder joint 82.

After navigating the length of the catheter 4 to the predetermined treatment site within the patient, the stent 100 may be deployed from the catheter 4 in a variety of ways. In one embodiment, the catheter 4 is retracted while maintaining the position of the core wire 41 to expose the distal end 27 of the delivery core wire 41 and the distal end 102 of the stent 100. Upon exiting the catheter 4, the portion of the stent 100 that is not situated between the protective coil 85 and the core wire 41 and that is not covered by the catheter 4 begins to expand radially. The catheter 4 may then be further retracted until enough of the stent 100 is exposed such that the expansion diameter of the stent 100 is sufficient to engage the walls of the vessel (not shown), such as a blood vessel. Upon engaging a portion of said vessel, the stent 100 may be at least partially anchored within the vessel.

The core wire 41 may then be rotated at its proximal end, which causes rotation at the distal end 27 relative to the stent 100. The rotation of the core wire 41 also causes twisting of the protective coil 85, which pushes the distal end 102 of the stent 100 out from beneath the protective coil 85 like a corkscrew. Once the distal end 102 of the stent 100 is released from the protective coil 85, it expands to engage the walls of the vessel. The catheter 4 may then be further retracted to expose and expand the remaining portions of the stent 100.

Those skilled in the art will readily recognize that variations of this deployment method are possible. For example, the catheter 4 may be further retracted before rotating the core wire 41, such as by expanding the proximal end 107 of the stent 100 before expanding the distal end 102. Other examples of deployment variations include causing or otherwise creating variable porosity of the stent 100.

Once the entire stent 100 is expanded, the core wire 41 may then be retracted back into the catheter 4 by pulling proximally on the core wire 41 and maintaining the catheter 4 in its position. The proximal taper of the solder joint 52 coupled to the proximal marker 88 helps guide retraction of the core wire 41 back into the catheter 4. The core wire 41 and the catheter 4 may then be both retracted from the vessel and vasculature of the patient.

In some aspects, embodiments disclosed herein provide stent delivery devices, as exemplified by shown in FIG. 2A, comprising a first retaining polymer 810 disposed about and retaining a self-expanding stent 805 at a proximal end 830, a second retaining polymer 820 disposed about and retaining the self-expanding stent at a distal end 840, a first resistance member 815 in thermal communication with first retaining polymer 810, and a second resistance member 825 in thermal communication with second retaining polymer 820. Second retaining polymer 820 and second resistance member 825 are configured to allow release and deployment of distal end 840 of self-expanding stent 805 without release of proximal end 830 of self-expanding stent 805 from first retaining polymer 810. The heat produced, for example, via resistive heating (also called ohmic heating) is proportional to the square of the current multiplied by the electrical resistance of the wire in accordance with Joule's First Law:

$$Q \alpha I2 \cdot R$$

wherein Q is the heat in joules, I is the current in amperes, and R is the resistance in ohms. Selectivity for release of distal end 840 of self-expanding stent 805 via resistive heating may be a function of the polymer selected in conjunction with calculations of the heat supplied according to Joule's First Law. Of the many advantages of selective release of one end of self-expanding stent 805 is the ability to fine tune the position of self-expanding stent 805, via catheter delivery, by pulling deployed distal end 840 back into the catheter to realign the stent. In this regard, self-expanding stent 805, the catheter, or both, may be further equipped with a radio-opaque fiducial marker to guide its placement.

Referring again to FIG. 2A, and with reference to FIG. 2B, first and second retaining polymer members 810 and 820 are configured hold stent 805 in place against forces inherent in self-expanding stent 805 that provide for self expansion and longitudinal contraction upon up release from the device. In operation, release of just distal end 840 from second retaining polymer member 820 may allow partial longitudinal contraction and initial expansion of self-expanding stent 805. The exact degree of radial expansion and/or longitudinal contraction may be mitigated by, inter alia, the presence or absence of a delivery catheter.

In some embodiments, stent delivery devices disclosed herein may further comprise a push wire 850 which can be used to guide the stent delivery device when in use. Push wire 850 may also be used to supply the requisite current to first resistance member 815, second resistance member 825, or both. In some embodiments, push wire 850 does not carry current to either resistance member. In other embodiments, push wire 850 may carry current to an electrode embedded with the wall of a delivery catheter for subsequent delivery to either or both resistance members 815 and/or 825. The distal end of push wire 850 may comprise a blunt atraumatic tip 860, as recognized by those skilled in the art.

First retaining polymer 810 and second retaining polymer 820 may comprise any thermoplastic or thermoset material, although the skilled artisan will recognize that for good melt characteristics, first retaining polymer 810 and second retaining polymer 820 may be beneficially a thermoplastic. Nonetheless, thermoset materials may be employed in devices disclosed herein. Thermoset materials may not have a true melting point, but may become more pliable/elastic and/or may decompose upon resistive heating, for example, to allow release at distal end 840 or proximal end 830 of self-expanding stent 805. In this regard, the material may be more accurately characterized by its softening point (Vicat softening point as described herein below). In some embodiments, distal end 840 is a thermoplastic and proximal end 830 is a thermoset material. In some embodiments, distal end 840 is a thermoplastic and proximal end 830 is also a thermoplastic. In some embodiments, distal end 840 is a thermoset material and proximal end 830 is a thermoplastic. In some embodiments, distal end 840 and proximal end 830 are both thermoset materials.

Thermoplastic polymers may include, without limitation, acrylonitrile butadiene styrene (ABS), acrylic-based polymers such as PMMA, celluloid, cellulose acetate, cyclic olefin copolymer (COC), ethylene-vinyl acetate (EVA), ethylene vinyl alcohol (EVOH), fluoroplastics, such as PTFE, FEP, PFA, CTFE, ECTFE, and ETFE, ionomers, KYDEX™, an acrylic/polyvinyl chloride (PVC) alloy, liquid crystal polymer (LCP), polyoxymethylene (POM or acetal), polyacrylates, polyacrylonitrile (PAN or acrylonitrile), polyamide (PA or Nylon), polyamide-imide (PAI), polyaryletherketone (PAEK or Ketone), polybutadiene (PBD), polybutylene (PB), polybutylene terephthalate (PBT), polycaprolactone (PCL), polychlorotrifluoroethylene (PCTFE), polyethylene terephthalate (PET), polycyclohexylene dimethylene terephthalate (PCT), polycarbonate (PC), polyhydroxyalkanoates (PHAs), polyketone (PK), polyester, polyethylene (PE), polyetheretherketone (PEEK), polyetherketoneketone (PEKK), polyetherimide (PEI), polyethersulfone (PES), chlorinated polyethylene (CPE), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polytrimethylene terephthalate (PTT), polyurethane (PU), polyvinyl acetate (PVA), polyvinyl chloride (PVC), polyvinylidene chloride (PVDC), ptyrene-acrylonitrile (SAN), and combinations thereof. Any of the aforementioned thermoplastics may be combined/coextruded in any combination of two, three, four, or more thermoplastic materials to tailor to desired melting characteristics. As will be recognized by the skilled artisan, the exact selection of a thermoplastic may depend on, inter alia, the heat supplied by resistive heating of first resistance member 815 and/or second resistance member 825, and safety factors of the material employed in the area where the stent is intended to be deployed. Thermoplastic materials may be integrated into device 800 via melt forming about distal end 840 and/or proximal end 830 of self-expanding stent 805.

Thermoset polymers may include, without limitation, phthalic/maelic type polyesters, vinyl esters, epoxies, phenolics, phenol-formaldehyde, cyanates, cyanate esters, polycyanurates, bismaleimides, polyimides, nadic end-capped polyimides, such as PMR-15, duroplast, urea-formaldehyde, melamine, and combinations thereof. As with thermoplastic materials, safety and the ability to release the one of the two stent ends may factor into the exact choice of a thermoset material. Thermoset materials may be integrated with the device by standard methods known in the art such as injection or compression molding, for example.

Figure 3A:
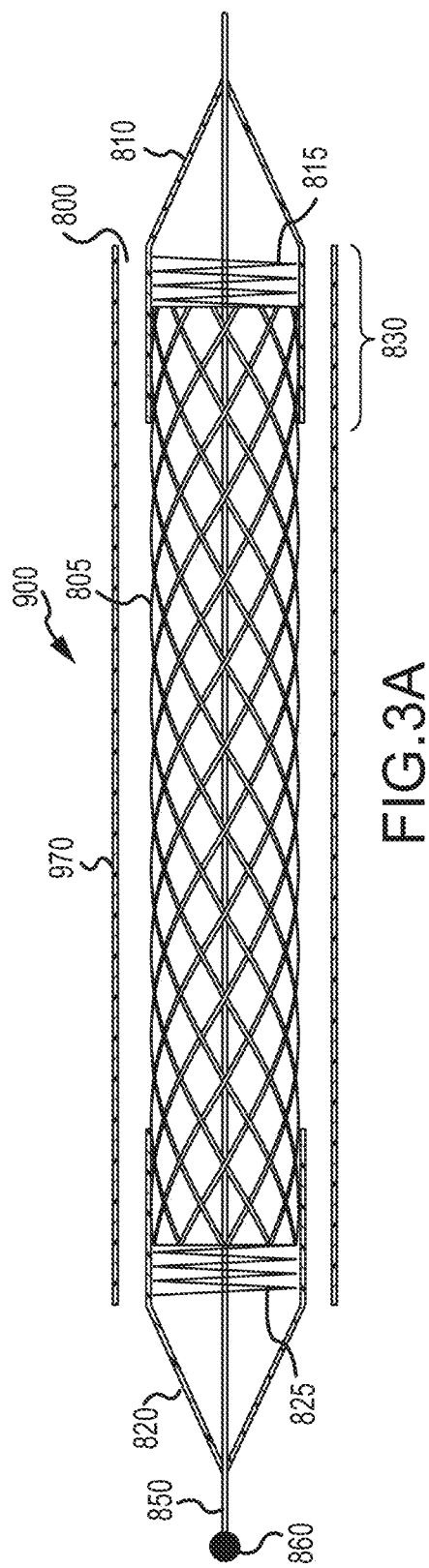
FIG. 3A shows a system comprising the delivery device of FIG. 2A disposed within a catheter, the device having a guidewire to longitudinally position the delivery device.

In some embodiments, second retaining polymer 820 and second resistance member 825 are configured to allow release and deployment of distal end 840 of self-expanding stent 805 without release of proximal end 830 of self-expanding stent 805 from first retaining polymer 810. Such selective release of distal end 840 may allow for repositioning of the stent via reversible re-entry into a delivery catheter. FIG. 3A shows an example of device 800 disposed within a delivery catheter 970.

Figure 3B:
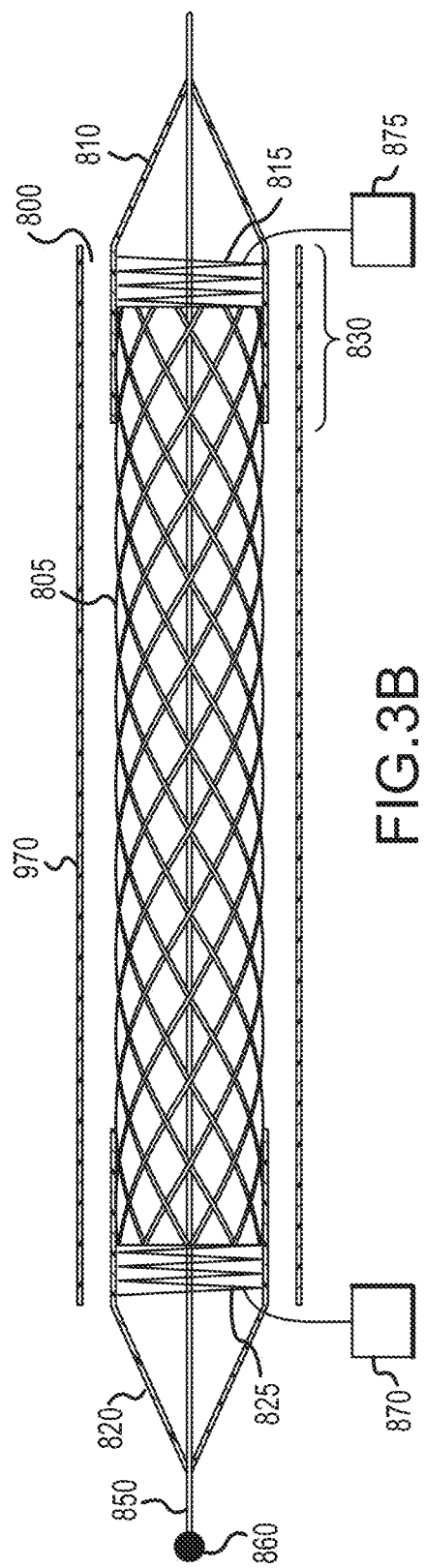
FIG. 3B shows the system of FIG. 3A generically attached to separate power sources for selective and separate delivery of a current to the first and second retaining polymer members. One source may be the guidewire, while another source may be an electrode disposed in the wall of the catheter.

In some such embodiments, stent delivery devices disclosed herein may be provided with current that is independently deliverable to first resistance member 815 and second resistance member 825, as indicated generically in FIG. 3B. FIG. 3B shows a distal power source 870 configured to be in electronic communication with second resistance member 825 and a proximal power source 875 configured to be in electronic communication with first resistance member 815. In some embodiments, distal power source 870 may be provided by an electrode embedded in the wall of the catheter. In some embodiments, distal power source 870 may be provided by splitting of a wire bundle off guidewire 850. In some embodiments, differential delivery of current may be achieved, for example, via delivery to one resistance member via push wire 850 and the other resistance member via, for example, an electrode disposed on a wall of delivery catheter 970. Thus, for example, release of second retaining polymer 820 may be selectively achieved by supplying delivery catheter 970 with a current to resistively heat second resistance member 825, while release of first retaining polymer 810 may be achieved via current delivery via push wire 850 which may resistively heat first resistance member 815. In such a configuration, it may be beneficial to electrically isolate second resistance member 825 from push wire 850.

In some embodiments, push wire 850 may comprise a plurality of wires in a bundle wherein a first portion of the bundle of wires may selectively deliver a current to second resistance member 825 and a second portion of the bundle of wires may selectively deliver a current to first resistance member 815. In some embodiments, selective delivery of current to first resistance member 815 and second resistance member 825 may be achieved via separately positioned electrodes within the wall of a delivery catheter 970. In some embodiments, a single electrode within delivery catheter 970 may be positioned to provide a current to second resistance member 825, and after properly aligning the stent into position, the same electrode may be re-aligned to deliver a current to first resistance member 815. In some embodiments, a single current source may be split to deliver a greater current to second resistance member 825. In such a situation, when the resistance of second resistance member 825 and first resistance member 815 are the same, more heat will be generated at second resistance member 825, according to Joule's First law.

In some embodiments, stent delivery devices disclosed herein may have a thickness of the second retaining polymer that is less than the thickness of first retaining polymer such that application of a current, including the same current source, to the first and second resistance members, 815 and 825, respectively, results in selective rapid melting of the second retaining polymer 820. In some such embodiments, the thickness of the polymer alone may provide the requisite removal selectivity and the first retaining polymer 810 and second retaining polymer 820 may comprise the same material. In other embodiments, the thickness of second retaining polymer 820 may be less than the thickness of first retaining polymer 810 and the materials making up the two retaining polymers may further differ in melting points. In such a configuration, the differences in melting point and thickness of the material may synergistically provide the requisite selectively for removing second retaining polymer 820 from distal end 840. Where the materials employed may have differing melt characteristics, by way of differing melting points, differing thickness, or combinations thereof, the resistance of first resistance member 815 and second resistance member 825, may be in a range from about 50 ohms to about 20 megaohms, with an applied current in a range from about 10 microamps to about 20 amps.

In some embodiments, stent delivery devices disclosed herein may have a resistance of second resistance member 825 that is higher than the resistance of first resistance member 815. Thus, for example, a single current may be supplied to both first resistance member 815 and second resistance member 825 via electrical contact with push wire 850, which is itself supplied with a current. Thus, the resistive heating supplied by second resistance member 825 to second retaining polymer 820 may be greater than the resistive heating supplied by first resistance member 815 to first retaining polymer 810. Thus, by judicious choice of melting point (or softening point) of the polymer material of first retaining polymer 810 and second retaining polymer 820, a specific current and resistance may be applied to first resistance member 815 and/or second resistance member 825 to effect the release of proximal end 830 or distal end 840 with the desired selectivity. As used herein, the term "melting point" generally refers to a thermoplastic polymer and represents the temperature at which the solid phase and liquid phase of the polymer coexist in equilibrium. As used herein, the term "softening point" may be used to generally refer to the relaxation of a polymer, such as a thermoset, which does not have a true melting point, but nonetheless becomes more pliable with heating. In some such embodiments, the "softening point" may be the softening point as recognized by those skilled in the art of plastics. Standards to determine Vicat softening point include, but are not limited to, ASTM D 1525 and ISO 306.

In an ohmic heating regime employing second resistive member 825 having a resistance higher than first resistance member 815, the resistance of the second resistance member may be in a range from about 50 ohms to about 20 megaohms, with an applied current in a range from about 10 microamps to about 20 amps. By way of example, release of distal end 840 may be achieved with a current of 10 microamps, and resistance of 20 megaohms, employing a polymer material for second retaining polymer such as low-melting polymers and low-melting polymer blends.

In some embodiments, stent delivery devices 800 disclosed herein may provide first retaining polymer 810 and second retaining polymer 820 having different melting points. In some embodiments, under the operating conditions for deployment of distal end 840 and proximal end 830, the melting points of the retaining polymer may be in a range from about 40° C. to about 100° C.

In some aspects, embodiments disclosed herein provide a system 900, as shown in FIG. 3A, for stent delivery comprising a catheter 970, a stent deliver device 800 comprising a first retaining polymer 810 disposed about and retaining a self-expanding stent 805 at a proximal end 830, a second retaining polymer 820 disposed about and retaining the self-expanding stent 805 at a distal end 840, a first resistance member 815 in thermal communication with first retaining polymer 810, and a second resistance member 825 in thermal communication with second retaining polymer 820, second retaining polymer 820 and second resistance member 825 are configured to allow release and deployment of distal end 840 of self-expanding stent 805 without release of proximal end 830 of self-expanding stent 805 from first retaining polymer 810, and system 900 further comprising a push wire 850, extending through the lumen of the self-expanding stent 805, push wire 850 being capable of delivering a current to first resistance member 815, second resistance member 825, or combinations thereof.

In some embodiments, system 900 disclosed herein may deploy distal end 840 of self-expanding stent 805 in a reversible manner by pulling the self-expanding stent 805 back into catheter 970, even in the event where the catheter has been initially removed from the system during deployment. By drawing released distal end 840 back into catheter 970 allows for repositioning of the stent. In some embodiments, system 900 disclosed herein may employ a current that is independently deliverable to first resistance member 815 and second resistance member 825. As described above, this may be achieved by delivery of current to push wire 850, one or more electrodes disposed within the wall of catheter 970, or combinations thereof.

In some embodiments, first retaining polymer 810 and second retaining polymer 820 may be disposed about self-expanding stent 805 in a manner such that self-expanding stent 805 is under a tension and elongated relative to the fully deployed state. Push wire 850 may also provide an attachment point at each end of self-expanding stent 805 to which first retaining polymer 810 and second retaining polymer 820 are attached and held in apart prior to deployment. Referring to FIGS. 4A and 4B, there is shown device 800 before (4A) and after (4B) release of distal end 840 from second retaining polymer 820. Note that, in use, delivery catheter 970 may or may not be present during deployment of distal end 840. That is, delivery catheter 970 may be present at the site of released distal end 840 or not. In some embodiments, delivery catheter 970 may be absent at the site of released distal end 840, but still present over at least a portion of device 800. In other embodiments, delivery catheter may be completely removed from device 800 during deployment, as shown in FIGS. 4A and 4B. After release of distal end 840, self-expanding stent 805 may contract longitudinally while also expanding to greater diameter, as shown in FIG. 4B. Likewise the melting of second retaining polymer 820 may be accompanied by curling or shrinking of the polymer material to aid in release of distal end 840. In some embodiments, system 900 may include a stent 805 having fiducial marker that indicates the successful release of the distal end 840 of self-expanding stent 805.

Further in accordance with embodiments describing device 800 above, system 900 may employ a thickness of second retaining polymer 820 that is less than a thickness of first retaining polymer 810 such that application of a current to the first and second resistance members, 815 and 825, respectively, results in selective rapid melting of second retaining polymer 820 selectively over first retaining polymer 810. In some embodiments, the thickness of first retaining polymer 810 may be in a range from about 10 microns to about 2 mm, including all values in between and fractions thereof. In some embodiments, the thickness of second retaining polymer 820 may be in a range from about 10 microns to about 2 mm, including all values in between and fractions thereof. In some embodiments, system 900 employing selective release of distal end 840 on the basis of having a thickness differential may be characterized by a difference in thickness of first retaining polymer 810 and second retaining polymer 820 in a range from about 1 micorn to about 2 mm.

Further in accordance with embodiments describing device 800, system 900 may also provide the first retaining polymer and second retaining polymer having different melting points. In some embodiments, system 900 having differing melting point retaining polymers, a differential in melting point between the two polymers may be in a range from about 5° C. to about 40° C., including any value in between or fractions thereof. Consistent with embodiments disclosed herein, combinations of melting point differentials and polymer thicknesses may be employed to provide a system capable of selective deployment of distal end 840.

In some embodiments, system 900 may provide a resistance of second resistance member 825 that is higher than the resistance of first resistance member 815, as described above. The resistance members may be wire or ribbon in straight or coiled form. In some embodiments, differential resistance may be provided by providing different materials.

In some embodiments, first and second resistance members 815, 825 may comprise any material known in the art including, without limitation, KANTHAL™ (FeCrAl), nichrome 80/20, cupronickel (CuNi) alloys, and the like. In some embodiments, first and/or second resistance members 815, 825 may be in electrical communication with push wire 850. In some such embodiments, first and/or second resistance members 815, 825 may be attached to push wire 850 via a solder weld, for example.

Finally, in some embodiments, system 900 may further comprise one or more power sources for delivering a current to first resistance member 815 and second resistance member 825. The power source may deliver current in a constant manner or may be pulsed. In some embodiments, the power source may be beneficially in electronic communication with distal end 840 to provide a signal to terminate delivery of current to the system to assure that proximal end 830 remains attached to self-expanding stent 805 to allow for any necessary readjustment of the positioning of the stent 805. Such repositioning may be needed, for example, due to the concomitant contraction of self-expanding stent 805 upon release of distal end 840. In some embodiments, the signal to terminate delivery of current may include detection of a change in position of a fiducial marker on self-expanding stent 805.

In some aspects, embodiments disclosed herein provide methods of delivering a stent comprising: introducing a stent delivery device via catheter to a desired treatment location in a subject, the stent delivery device comprising a first retaining polymer disposed about and retaining a self-expanding stent at a proximal end, a second retaining polymer disposed about and retaining the self-expanding stent at a distal end, a first resistance member in thermal communication with the first retaining polymer, and a second resistance member in thermal communication with the second retaining polymer, wherein the second retaining polymer and second resistance member are configured to allow release and deployment of the distal end of the self-expanding stent without release of the proximal end of the self-expanding stent from the first retaining polymer, and the method further comprising applying a current to the second resistance member to release and deploy the distal end of the self-expanding stent.

Referring now to FIGS. 5A-D, there is shown a method 1000 for delivering a self-expanding stent 805. At step 1010, FIG. 5A, device 800 is introduced, via catheter 970 of system 900, to a desired treatment location 999 in a subject. At step 1020, FIG. 5B, distal end 840 is released from second retaining polymer 820. In some embodiments, this release is conducted as shown in FIG. 5B, in the presence of catheter 970. In other embodiments, release of distal end 840 may be conducted in the absence of delivery catheter 970 to deploy directly the distal end treatment location 999. In some embodiments, methods of delivering a stent disclosed herein may optionally comprise adjusting deployed distal end 840 of self-expanding stent 805 by pulling the self-expanding stent 805 back into the catheter 970, if not within the catheter during deployment. After readjustment of released distal end 840 the catheter may be removed to redeploy the stent as shown in step 1030, FIG. 5C. At this point, released distal end 840 may be expanded and in contact with a portion just beyond the distal end of treatment location 999. Because first retaining polymer 810 is still attached to the stent, the operator has the continuing option to reintroduce delivery catheter 970 to make any further positioning adjustments to self-expanding stent 805 as necessary. At this stage step 1040, FIG. 5D, may be performed to release proximal end 830 of the self-expanding stent 805 by supplying a current to the first resistance member 815. Again, while FIG. 5C shows the release absent catheter 970, one skilled in the art will recognize that release of proximal end 830 may be performed while delivery catheter 970 is still present, as in FIG. 5B. The fully deployed stent 805 in step 1040, FIG. 5D, may be contracted longitudinally relative to stent 805 still disposed within device 800.

Methods of deploying self-expanding stent 805 may include selective release of distal end 840 consistent with embodiments disclosed herein. Thus, in some embodiments, methods of delivering a stent disclosed herein may provide a current that is independently deliverable to the first resistive member and second resistive member. Further, in some embodiments, methods of delivering a stent disclosed herein may provide a thickness of the second retaining polymer that is less than a thickness of first retaining polymer such that application of a current to the first and second resistance members results in selective rapid melting of the second retaining polymer. In yet further embodiments, methods of delivering a stent disclosed herein may provide the resistance of the second resistance member that is higher than the resistance of the first resistance member. In still further embodiments, methods of delivering a stent disclosed herein may provide the first retaining polymer and second retaining polymer have different melting points. Any of the foregoing features may be used in any combination to effect selective release of distal end 840.

In some aspects, embodiments disclosed herein provide a method of treating an aneurysm, which is also represented by FIGS. 5A-D, comprising introducing a stent delivery device via catheter in the vicinity of an aneurysm in a subject; said stent delivery device comprising a first retaining polymer disposed about and retaining a self-expanding stent at a proximal end, a second retaining polymer disposed about and retaining the self-expanding stent at a distal end, a first resistance member in thermal communication with the first retaining polymer, and, a second resistance member in thermal communication with the second retaining polymer, wherein the second retaining polymer and second resistance member are configured to allow release and deployment of the distal end of the self-expanding stent without release of the proximal end of the self-expanding stent from the first retaining polymer, and the method further comprising applying a current to the second resistance member to release and deploy the distal end of the self-expanding stent.

Consistent with methods of delivering a stent to a desired treatment location, in some embodiments, methods of treating an aneurysm may further comprise adjusting the deployed distal end of the self-expanding stent by pulling the self-expanding stent into the catheter. In yet further embodiments, methods of treating an aneurysm may further comprise removing the catheter to redeploy the stent. In still further embodiments, methods of treating an aneurysm may further comprise deploying the proximal end of the self-expanding stent by supplying a current to the first resistance member.

Methods of deploying self-expanding stent 805 to treat an aneurysm may include selective release of distal end 840 consistent with embodiments disclosed herein. Thus, in some embodiments, methods of treating an aneurysm may provide a current that is independently deliverable to the first resistance member 815 and second resistance member 825. In some embodiments, methods of treating an aneurysm may provide a thickness of second retaining polymer 820 that is less than a thickness of first retaining polymer 810 such that application of a current to the first and second resistance members results in selective rapid melting of the second retaining polymer 820. In some embodiments, methods of treating an aneurysm may provide the resistance of second resistance member 825 that is higher than the resistance of the first resistance member 815. In some embodiments, methods of treating an aneurysm may provide first retaining polymer 810 and second retaining polymer 820 having different melting points. Any of the foregoing features may be used in any combination to effect selective release of distal end 840 to treat an aneurysm.

In some embodiments, methods of deploying self-expanding stent to treat an aneurysm may further include introducing a stent having a drug coating. In some such embodiments, the drug coating may release a drug in a controlled manner to block cell proliferation and reduce or prevent fibrosis and clotting associated with restenosis. In some embodiments, methods of deploying a self-expanding stent to treat an aneurysm may further include introducing a treatment agent directly into the stented aneurysm.

The apparatus and methods discussed herein are not limited to the deployment and use of an occluding device or stent within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component, or method step is intended to be dedicated to the public regardless of whether the element, component, or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A system for stent delivery, the system comprising:
  a self-expanding stent having a proximal end portion, a distal end portion, and a lumen;
  a push wire extending through the lumen;
  a first retaining polymer (a) in direct contact with the push wire and (b) disposed about and retaining the proximal end portion in a compressed configuration;
  a second retaining polymer (a) in direct contact with the push wire and (b) disposed about and retaining the distal end portion in a compressed configuration;
  a first resistance member in thermal communication with the first retaining polymer; and
  a second resistance member in thermal communication with the second retaining polymer;
  wherein the second retaining polymer is releasable from the stent independently of release of the first retaining polymer from the stent.

2. The system of claim 1, wherein the distal end portion can be compressed, after expanding from the compressed configuration to an expanded configuration, by pulling the distal end portion into a catheter.

3. The system of claim 1, wherein the first retaining polymer is configured to disengage from the stent in response to a first level of applied current, and the second retaining polymer is configured to disengage from the stent in response to a second level of applied current, the second level being different from the first level.

4. The system of claim 3, wherein the applied current is independently deliverable to the first resistance member and the second resistance member.

5. The system of claim 1, wherein a thickness of the second retaining polymer is less than a thickness of the first retaining polymer, such that application of a current to the first resistance member and the second resistance member results in severance of the second retaining polymer prior to severance of the first retaining polymer.

6. The system of claim 1, wherein an electrical resistance of the second resistance member is higher than an electrical resistance of the first resistance member.

7. The system of claim 1, wherein the first retaining polymer and the second retaining polymer have different melting points.

8. The system of claim 1, wherein each of the first retaining polymer and the second retaining polymer is configured to remain in direct contact with the push wire after disengagement from the stent.

9. A method of delivering a stent, the method comprising:
  introducing a stent delivery device via a catheter to a desired treatment location in a subject, the stent delivery device comprising:
    a first retaining polymer (a) in direct contact with a push wire and (b) disposed about and retaining a proximal end portion of a self-expanding stent when the stent is in a compressed configuration;
    a second retaining polymer (a) in direct contact with the push wire and (b) disposed about and retaining a distal end portion of the self-expanding stent in the compressed configuration;
    a first resistance member in thermal communication with the first retaining polymer; and
    a second resistance member in thermal communication with the second retaining polymer;
    wherein the second retaining polymer and the second resistance member are configured to permit expansion of the distal end portion of the self-expanding stent to an expanded configuration without expansion of the proximal end portion of the self-expanding stent;
  applying a current to the second resistance member to release and expand the distal end portion.

10. The method of claim 9, further comprising compressing the expanded distal end portion of the self-expanding stent by pulling the self-expanding stent into the catheter.

11. The method of claim 10, further comprising withdrawing the catheter relative to the stent to re-expand the stent.

12. The method of claim 9, further comprising expanding the proximal end of the self-expanding stent by supplying a current to the first resistance member.

13. The method of claim 9, wherein a current is independently deliverable to the first resistance member and the second resistance member.

14. The method of claim 9, wherein a thickness of the second retaining polymer is less than a thickness of the first retaining polymer, such that application of a same current to the first resistance member and the second resistance member results in severance of the second retaining polymer before severance of the first retaining polymer.

15. The method of claim 9, wherein an electrical resistance of the second resistance member is greater than an electrical resistance of the first resistance member.

16. The method of claim 9, wherein the first retaining polymer and the second retaining polymer have different melting points.

17. The method of claim 9, wherein the desired treatment location comprises an aneurysm.

18. The method of claim 9, wherein the second retaining polymer is in direct contact with the push wire after release from the distal end portion.

* * * * *